United States Patent
Zimlich, Jr. et al.

(10) Patent No.: US 6,796,303 B2
(45) Date of Patent: *Sep. 28, 2004

(54) PULMONARY AEROSOL DELIVERY DEVICE AND METHOD

(75) Inventors: William C. Zimlich, Jr., Dublin, OH (US); James E. Dvorsky, Norwich Township, OH (US); David R. Busick, Lewis Center, OH (US); Richard D. Peters, Gawanna, OH (US)

(73) Assignee: Battelle Pulmonary Therapeutics, Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/161,545

(22) Filed: Jun. 3, 2002

(65) Prior Publication Data

US 2002/0153006 A1 Oct. 24, 2002

Related U.S. Application Data

(63) Continuation of application No. 09/469,042, filed on Dec. 21, 1999, now Pat. No. 6,397,838, which is a continuation-in-part of application No. 09/220,249, filed on Dec. 23, 1998, now abandoned.

(51) Int. Cl.$^7$ ............................................. A61M 11/00
(52) U.S. Cl. .............................. 128/200.14; 128/200.23
(58) Field of Search ...................... 128/200.14, 200.16, 128/200.23, 203.12, 203.24, 204.25; 239/332, 349, 704, 706, 708, 690, 695, 696, 699; 222/636; 604/58

(56) References Cited

U.S. PATENT DOCUMENTS

| | | | | |
|---|---|---|---|---|
| 4,790,479 A | * | 12/1988 | Matsumoto et al. ...... 239/102.2 |
| 5,511,726 A | * | 4/1996 | Greenspan et al. ...... 239/102.2 |
| 5,743,251 A | * | 4/1998 | Howell et al. ......... 128/200.14 |
| 5,894,841 A | * | 4/1999 | Voges ..................... 128/203.12 |
| 5,915,377 A | * | 6/1999 | Coffee .................... 128/200.16 |
| 6,068,199 A | * | 5/2000 | Coffee ............................ 239/3 |
| 6,105,571 A | * | 8/2000 | Coffee .................... 128/200.14 |
| 6,116,516 A | * | 9/2000 | Ganan-Calvo ................. 239/8 |
| 6,158,431 A | * | 12/2000 | Poole .................... 128/203.12 |
| 6,227,466 B1 | * | 5/2001 | Hartman et al. ............ 239/704 |
| 6,275,650 B1 | * | 8/2001 | Lambert ..................... 392/395 |
| 6,290,685 B1 | * | 9/2001 | Insley et al. ................ 604/317 |
| 6,397,838 B1 | * | 6/2002 | Zimlich et al. ......... 128/200.14 |
| 6,454,193 B1 | * | 9/2002 | Busick et al. ............... 239/690 |

* cited by examiner

*Primary Examiner*—Teena Mitchell
(74) *Attorney, Agent, or Firm*—Porter, Wright, Morris & Arthur, LLP

(57) ABSTRACT

A device and method for delivering an aerosolized liquid having therapeutic properties to a user's lungs. The compact and convenient device includes a housing of such size that it can be held in a user's one hand with an exit opening in the housing for directing the aerosol to the user's mouth. The housing encloses a dispensing system for containing the liquid to be aerosolized and delivering it to an electrohydrodynamic apparatus and an electrohydrodynamic apparatus for aerosolizing the liquid and delivering the aerosol to the exit opening. The electrohydrodynamic apparatus produces a cloud of aerosolized liquid droplets having a monodispersed respirable droplet size and near zero velocity. The aerosolizing apparatus includes a plurality of spray sites each having a tip end, the spray sites cooperating with a charge source to result in an aerosolized spray from at least one tip end, a plurality of discharge electrodes downstream of the tip ends, and a plurality of reference electrodes downstream of the plurality of discharge electrodes.

42 Claims, 7 Drawing Sheets

PULMONARY AEROSOL DELIVERY DEVICE AND METHOD

BACKGROUND AND OBJECTS OF THE INVENTION

This is a continuation of U.S. application Ser. No. 09/469,042, filed Dec. 21, 1999, now U.S. Pat. No. 6,397,838 which is a continuation-in-part of U.S. application Ser. No. 09/220,249, filed Dec. 23, 1998, now abandoned, each of which is fully incorporated herein by reference.

This invention relates to devices and methods for delivering an aerosolized liquid to a user's lungs, and particularly an aerosolized liquid having therapeutic properties.

For some therapeutic agents, delivery of the aerosolized liquid without a propellant is preferred. Such liquids may be aerosolized, for example, by an electrohydrodynamic apparatus. The liquid to be aerosolized is made to flow over a region of high electric field strength, which imparts a net electric charge to the liquid. This electric charge tends to remain on the surface of the liquid such that, as the liquid exits the nozzle, the repelling force of the surface charge balances against the surface tension of the liquid, forming a cone (a "Taylor cone" as described in, e.g., M. Cloupeau and B. Prunet-Foch, "Electrohydrodynamic Spraying Functioning Modes: A Critical Review," *J. Aerosol Sci.*, Vol. 25, No. 6, pp. 1021, 1025–1026 (1994)). In the region of the tip of the cone, which has the greatest charge concentration, the electrical force exerted on the liquid surface overcomes the surface tension, generating a thin jet of liquid. The jet breaks into droplets of more or less uniform size, which collectively form a cloud that may be inhaled by a user to deliver the aerosol to the user's lungs.

Dr. Ronald Coffee of Oxford University, Oxford, England, has proposed and developed methods of aerosolizing pharmaceutical formulations and discharging the aerosol particles prior to their delivery to a user. One such method uses an electrohydrodynamic apparatus having a single spray site (nozzle) surrounded by four discharge electrodes and a grounded shield to produce a monodispersed spectrum of particle sizes.

Known pulmonary delivery devices that use electrohydrodynamic spraying are unwieldy and require connection to either an alternating current power supply or a large direct current power supply. These conventional devices are suitable for use in hospital or other clinical applications, such as for administering a therapeutic agent during a scheduled treatment appointment, but generally are not suitable for use directly by a user on a demand or as-needed basis outside a clinical setting. Conventional devices are particularly unsuited for use during a user's regular activities at home, at work, while traveling, and during recreational and leisure activities.

Known pulmonary delivery devices that use electrohydrodynamic spraying also lack a sufficient volumetric flow rate to deliver a desired amount of certain therapeutic liquids during the inhalation of one to two breaths by a user. Attempts to increase the flow rate generally have resulted in even more bulky devices unsuitable for hand-held use. These delivery devices also are not generally capable of spraying liquids having a broad range of conductivities.

It is an object of the invention to provide a device and method that conveniently delivers an aerosolized liquid to a user's lungs. It is another object of the invention to provide a compact, portable, hand-held pulmonary delivery device that may be used in a variety of indoor and outdoor locations. The device would allow users to administer therapeutic agents on an as-needed basis in nonclinical settings and provide advantages over conventional devices used by hospitals and clinicians.

It is a further object of the invention to provide a compact and convenient device and method that delivers an increased volumetric flow rate of liquid so that a desired amount of a therapeutic liquid dispersed into respirable particles may be administered during the inhalation of one to two breaths by a user.

It is another object of the invention to provide a device and method capable of electrohydrodynamic spraying of therapeutic liquids having a broad conductivity range in a compact and convenient device.

It is yet another object of the invention to provide an apparatus for aerosolizing liquid that is useful in the delivery to a user, in the form of respirable particles, of a desired amount of a therapeutic liquid within a broad conductivity range.

SUMMARY OF THE INVENTION

The invention described here provides a compact, convenient device and method for delivering an aerosolized liquid having therapeutic properties to a users lungs by electrohydrodynamic spraying. Preferably, the device is small enough that it can be comfortably carried by a user, for example, in shirt pocket or purse, and has a self-contained power supply so that it can be used anywhere. The device may be disposable or reusable.

In a preferred embodiment, the pulmonary aerosol delivery device comprises a housing sized so that it can be held in a user's hand and having an exit opening for directing the aerosol to the user's mouth. The housing encloses a dispensing system for containing the liquid to be aerosolized and delivering it to an electrohydrodynamic apparatus, an electrohydrodynamic apparatus for aerosolizing the liquid and delivering the aerosol to the exit opening; and a power supply system for providing sufficient voltage to the electrohydrodynamic apparatus to aerosolize the liquid. The power supply system may comprise a battery and a DC to DC high voltage converter so the device may be cordless.

The liquid to be aerosolized may comprise a drug. The dispensing system of the device may include a containment vessel for containing the drug, which may be a holder for a drug enclosed in single dose units, a plurality of sealed chambers each holding a single dose of a drug, or a vial for enclosing a bulk supply of a drug. The containment vessel may have antimicrobial properties and may be capable of maintaining the sterility of a sterile drug placed therein.

The dispensing system delivers a single dose of the drug from the containment vessel to the electrohydrodynamic apparatus, which may be accomplished using a metering system. The metering system may include a chamber for collecting a predetermined volume of liquid having an inlet communicating with the containment vessel and an outlet communicating with the electrohydrodynamic apparatus; a chamber housing above the chamber; a chamber housing spring adjacent to the chamber; and a button spring above the chamber housing. The button spring exerts a downward force against the chamber housing when an actuator button is depressed to force liquid in the chamber through the outlet and the chamber housing spring exerts an upward force against the chamber housing when the actuator button is released. The upward travel of the chamber housing induces a vacuum in the chamber to draw liquid from the containment vessel through the inlet. The chamber volume is controlled by an adjustable stop that limits the upward travel of the chamber housing. The metering system may further include check valves at the chamber inlet and outlet to provide unidirectional liquid flow.

The device may further include a control circuit communicating with the dispensing system, the electrohydrodynamic apparatus and the power supply system. The control circuit may include an on/off power indicator, a power save feature, or a lockout to prevent use by an unauthorized user.

The control circuit may include an actuation device for initiating the flow of aerosolized liquid. The actuation device may be a breath sensor for detecting a user's inhalation of one or more breaths, such as a flapper switch, a pressure transducer, an air motion detector, or an air velocity detector, which cooperates with the electrohydrodynamic apparatus to initiate the flow of aerosolized liquid. The actuation device also may be a manual actuator on the exterior of the housing.

The electrohydrodynamic apparatus of the device may be capable of aerosolizing the liquid at a flow rate of at least about 20 µL/sec. It also may be capable of aerosolizing the liquid into droplets such that at least about 80% of the droplets have a diameter of less than or equal to about 5 microns.

The housing of the device may have antimicrobial properties. The exit opening of the housing may be movable to assist in directing the aerosol to the user's mouth.

In another preferred embodiment, a pulmonary aerosol delivery device includes a housing sized so it can be held in a user's hand and having an exit opening for directing the aerosol to the user's mouth. The housing encloses a containment vessel holding a liquid to be aerosolized, an electrohydrodynamic apparatus for aerosolizing the liquid and delivering the aerosol to the exit opening, a power supply for providing sufficient voltage to the electrohydrodynamic apparatus to aerosolize the liquid, and a dispensing system for delivering the liquid to be aerosolized from the containment vessel to the electrohydrodynamic system.

The dispensing system may include a metering system for dispensing a desired amount of the liquid to the electrohydrodynamic apparatus, which may comprise a mechanically-actuated piston pump. The metering system and the control circuit may cooperate to provide a dose counter or a dose display, which may show the doses administered or the doses remaining. The control circuit may include a timer that cooperates to limit the delivery of the liquid by the metering system. The control circuit also may include a signal that cooperates with the timer to alert a user that a dose is due by an alarm or a visual display showing the time when the next dose is due. The control circuit includes a memory for storing dose information to be provided to the metering system or recording the dose history.

The electrohydrodynamic apparatus of the device may include a charge neutralizer for aiding in the delivery of the drug to a user's lungs. The electrohydrodynamic apparatus also may include a generally circular base plate having upper and lower surfaces; a plurality of spray sites arranged in a circular pattern along the perimeter of the lower surface of the base plate, each of the spray sites having a base end mounted to the base plate and a tip end oriented vertically downward; a skirt extending downward from the base plate; a plurality of discharge electrodes each extending radially inward from the skirt in the area of the spray site tip ends; and a plurality of reference electrodes each extending radially inward from the skirt downstream of and between the discharge electrodes. A dielectric material may be enclosed within the skirt or the skirt may be comprised of a dielectric material.

The tip end of at least one spray site may be chamfered. The exterior of at least one of the spray sites also may be coated with a low surface energy coating. The electrohydrodynamic apparatus further may include a manifold extending between the dispensing system and the base ends of the spray sites.

In another preferred embodiment, the pulmonary aerosol delivery device includes a housing sized so it can be held in a user's hand and having an exit opening for directing the aerosol to the user's mouth. The housing includes a dispensing system for containing the liquid to be aerosolized and delivering it to an electrohydrodynamic apparatus; an electrohydrodynamic apparatus for aerosolizing the liquid and delivering the aerosol to the exit opening; and a power supply system for providing sufficient voltage to the electrohydrodynamic apparatus to aerosolize the liquid. The electrohydrodynamic device includes a spray site having a sufficient electric field strength that a net electrical charge is imparted to the surface of a liquid flowing over the spray site, with the surface charge initially balancing the surface tension of the liquid to cause the liquid to form a cone and eventually overcoming the surface tension of the liquid in the region of the tip of the cone to generate a thin jet of liquid that breaks into droplets of respirable size.

In a preferred embodiment, the method of orally administering an aerosolized liquid therapeutic agent includes the steps of:

storing the liquid in a containment vessel;

dispensing the liquid from the containment vessel to an electrohydrodynamic apparatus;

electrically actuating the electrohydrodynamic apparatus to aerosolize the liquid;

metering a desired amount of liquid to be dispensed from the containment vessel to the electrohydrodynamic apparatus; and enclosing the containment vessel and electrohydrodynamic apparatus within a cordless housing of such size that it can be held in a user's one hand, the housing including an exit opening for directing the aerosol to the user's mouth.

In the above-described method, the treating step may include neutralizing the electrical charge imparted to the aerosolized liquid and the electrical actuation step may be initiated by a user's inhalation of breath.

In another preferred embodiment, the method for orally administering an aerosolized liquid therapeutic agent comprises the steps of:

storing the liquid in a containment vessel;

metering a desired amount of liquid to be dispensed from the containment vessel to the electrohydrodynamic apparatus;

dispensing the liquid from the containment vessel to an electrohydrodynamic apparatus;

electrically actuating the electrohydrodynamic apparatus to aerosolize the liquid;

treating the aerosolized liquid to modify an electrical charge imparted to the aerosolized liquid by the electrohydrodynamic apparatus; and enclosing the containment vessel and electrohydrodynamic apparatus within a cordless housing of such size that it can be held in a user's one hand, the housing including an exit opening for directing the aerosol to the user's mouth.

The electrical actuation step may be initiated by a user's inhalation of breath.

Another preferred embodiment of the pulmonary aerosol delivery device comprises a housing of such size that it can be held in a user's one hand, the housing having an exit opening for directing the aerosol to the user's mouth and including therein, a dispensing system for containing the liquid to be aerosolized and delivering it to an apparatus for aerosolizing the liquid; an apparatus for aerosolizing the liquid and delivering the aerosol to the exit opening; and a power supply system for providing sufficient voltage to the aerosolizing apparatus to aerosolize the liquid. The apparatus for aerosolizing the liquid comprises a plurality of spray sites each having a tip end, the spray sites cooperating with a charge source to result in an electrohydrodynamic spray from at least one tip end, a plurality of discharge electrodes downstream of the tip ends, and a plurality of reference electrodes downstream of the plurality of discharge electrodes.

The invention also encompasses an apparatus for aerosolizing a liquid. In one preferred embodiment, the aerosolizing apparatus comprises a plurality of spray sites each having a tip end, the spray sites cooperating with a charge source to result in an aerosolized spray from at least one tip end, a plurality of discharge electrodes downstream of the tip ends, and a plurality of reference electrodes downstream of the plurality of discharge electrodes. The apparatus also may include a charge source for charging the spray sites sufficiently to result in an electrohydrodynamic spray from at least one tip end.

The plurality of discharge electrodes and the plurality of reference electrodes may be oriented toward the aerosolized spray and particularly may be oriented radially toward the aerosolized spray. Preferably, the plurality of discharge electrodes are spaced equidistant from one another and the plurality of reference electrodes are located in the interstices between the discharge electrodes.

The aerosolizing apparatus also may include a dielectric material between the plurality of discharge electrodes and the plurality of reference electrodes. The reference electrodes may extend through slots provided in the dielectric material.

Preferably, at least one of the plurality of spray sites has a sufficient electric field strength that a net electrical charge is imparted to the surface of a liquid flowing over the spray site such that the surface charge initially balances the surface tension of the liquid to cause the liquid to form a cone and eventually overcomes the surface tension of the liquid in the region of the tip of the cone to generate a thin jet of liquid that breaks into aerosolized droplets of respirable size. At least one of the plurality of discharge electrodes may have a sufficient electric field strength to substantially neutralize a charge on the aerosolized droplets generated by the spray site.

The tip ends of the plurality of spray sites may be oriented vertically downward. Preferably, the plurality of spray sites are arranged in a generally circular pattern and are spaced equidistant from one another. The tip end of at least one of the plurality of spray sites may be chamfered. Also, the exterior of at least one of the plurality of spray sites may be coated with a low surface energy coating.

Another preferred aerosolizing apparatus comprises a tubular base having a generally circular cross-section, a plurality of spray sites each having a tip end extending axially into a first end of the base, the spray sites cooperating with a charge source to result in an aerosolized spray from at least one tip end, a plurality of discharge electrodes each connected to the interior of the base downstream of the spray sites, and a plurality of reference electrodes each connected to the interior of the base downstream of the plurality of discharge electrodes. The apparatus may further include a charge source for charging the spray sites sufficiently to result in an electrohydrodynamic spray from at least one tip end.

Preferably, the plurality of discharge electrodes and the plurality of reference electrodes are oriented toward the aerosolized spray. The plurality of discharge electrodes may be located in the area of the tip ends of the plurality of spray sites.

In the above-described aerosolizing apparatus, at least one of the plurality of spray sites preferably has a sufficient electric field strength that a net electrical charge is imparted to the surface of a liquid flowing over the spray site such that the surface charge initially balances the surface tension of the liquid to cause the liquid to form a cone and eventually overcomes the surface tension of the liquid in the region of the tip of the cone to generate a thin jet of liquid that breaks into aerosolized droplets of respirable size. At least one of the plurality of discharge electrodes may have a sufficient electric field strength to substantially neutralize a charge on the aerosolized droplets generated by the spray site.

The plurality of reference electrodes and the plurality of discharge electrodes may extend radially inwardly from the interior of the base. The plurality of discharge electrodes preferably are spaced equidistant from one another and the plurality of reference electrodes are located in the interstices between the discharge electrodes.

The aerosolizing apparatus also may include a dielectric material within the base between the discharge electrodes and the reference electrodes. Preferably, the reference electrodes extend through slots provided in the dielectric material.

The tip ends of the plurality of spray sites provided in the aerosolizing apparatus preferably are oriented vertically downward. The plurality of spray sites may be arranged in a predetermined pattern, and particularly in a generally circular pattern.

In yet another preferred embodiment, the aerosolizing apparatus comprises a generally circular base plate having upper and lower surfaces, a plurality of spray sites arranged in a circular pattern along the perimeter of the lower surface of the base plate, each of the spray sites having a base end mounted to the base plate and a tip end, the spray sites cooperating with a charge source to result in an aerosolized spray from at least one tip end, a skirt extending downward from the base plate, a plurality of discharge electrodes each extending from the skirt downstream of the spray site tip ends; a plurality of reference electrodes each extending from the skirt downstream of the discharge electrodes, and a dielectric material between the plurality of discharge electrodes and the plurality of reference electrodes. The dielectric material may be a discrete member provided within the skirt or the skirt may be comprised of a dielectric material. The aerosolizing apparatus also may include a charge source for charging the spray sites sufficiently to result in an electrohydrodynamic spray from at least one tip end.

The plurality of reference electrodes may be positioned in interstices between the discharge electrodes. Preferably, the plurality of discharge electrodes are spaced equidistant from one another with the plurality of reference electrodes are located in the interstices between the discharge electrodes. The reference electrodes may extend through slots provided in the dielectric material.

In the above-described aerosolizing apparatus, at least one of the plurality of spray sites preferably has a sufficient electric field strength that a net electrical charge is imparted to the surface of a liquid flowing over the spray site such that the surface charge initially balances the surface tension of the liquid to cause the liquid to form a cone and eventually overcomes the surface tension of the liquid in the region of the tip of the cone to generate a thin jet of liquid that breaks into droplets of respirable size. At least one of the plurality of discharge electrodes may have a sufficient electric field strength to substantially neutralize a charge on the aerosolized droplets generated by the spray site.

These and further objects of the invention will become apparent from the following detailed description.

DETAILED DESCRIPTION OF THE PREFERRED EMBODIMENTS

Figure 1:
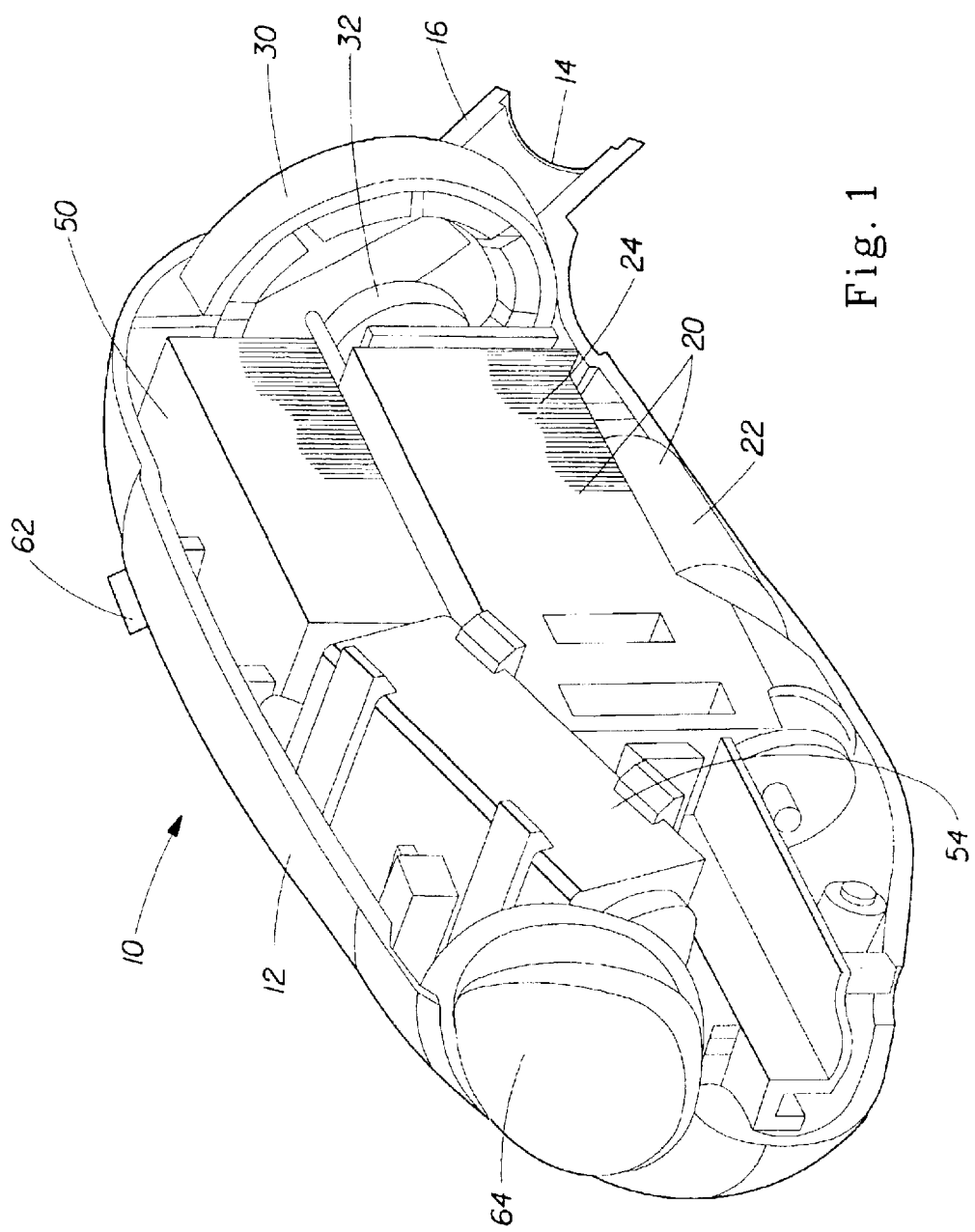
FIG. 1 is a perspective view of a device of the present invention with a top portion of the housing removed.

The invention described here provides a compact, convenient apparatus for delivering an aerosolized liquid having therapeutic properties to a user's lungs. The hand-held pulmonary drug delivery device efficiently aerosolizes a therapeutic liquid into droplets of respirable size and administers a clinically relevant dose of a variety of therapeutic liquids to a user.

Liquids amenable to aerosolization by electrohydrodynamic spraying generally are characterized by particular electrical and physical properties. Without limiting the scope of the invention, liquids having the following electrical and physical characteristics permit optimum performance by the device and method to generate a clinically relevant dose of respirable particles within a few seconds. The surface tension of the liquid typically is in the range of about 15–50 dynes/cm, preferably about 20–35 dynes/cm, and more preferably about 22–33 dynes/cm. Liquid resistivity typically is greater than about 200 ohm-meters, preferably greater than about 250 ohm-meters, and more preferably greater than about 400 ohm-meters. The relative electrical permittivity typically is less than about 65, preferably less than about 45. Liquid viscosity typically is less than about 100 centipoise, preferably less than about 50 centipoise. Although the above combination of characteristics allows optimum performance, it may be possible to effectively spray liquids with one or more characteristics outside these typical values using the device and method of the invention. For example, certain nozzle configurations may allow effective spraying of less resistive (more conductive) liquids.

Therapeutic agents dissolved in ethanol generally are good candidates for electrohydrodynamic spraying because the ethanol base has a low surface tension and is nonconductive. Ethanol also is an antimicrobial agent, which reduces the growth of microbes within the drug formulation and on the housing surfaces. Other liquids and solvents for therapeutic agents also may be delivered using the device and method of the invention. The liquids may include drugs or solutions or microsuspensions of drugs in compatible solvents.

As described above, the electrohydrodynamic apparatus aerosolizes the liquid by causing the liquid to flow over a region of high electric field strength, which imparts a net electric charge to the liquid. In the present invention, the region of high electric field strength typically is provided by a negatively charged electrode within the spray nozzle. The negative charge tends to remain on the surface of the liquid such that, as the liquid exits the nozzle, the repelling force of the surface charge balances against the surface tension of the liquid, forming a Taylor cone. The electrical force exerted on the liquid surface overcomes the surface tension at the tip of the cone, generating a thin jet of liquid. This jet breaks into droplets of more or less uniform size, which collectively form a cloud.

The device produces aerosolized particles of respirable size. Preferably, the droplets have a diameter of less than or equal to about 6 microns, and more preferably, in the range of about 1–5 microns, for deep lung administration. Because many formulations are intended for deep-lung deposition, at least about 80% of the particles preferably have a diameter of less than or equal to about 5 microns for effective deep lung administration of the therapeutic agent. The aerosolized droplets are substantially the same size and have near zero velocity as they exit the apparatus.

The range of volumes to be delivered is dependent on the specific drug formulation. Typical doses of pulmonary therapeutic agents are in the range of 0.1–100 $\mu$L. Ideally, the dose should be delivered to the patient during a single inspiration, although delivery during two or more inspirations may be acceptable under particular conditions. To achieve this, the device generally must be capable of aerosolizing about 0.1–50 $\mu$L, and particularly about 10–50 $\mu$L, of liquid in about 1.5–2.0 seconds. Delivery efficiency is also a major consideration for the pulmonary delivery device so liquid deposition on the surfaces of the device itself should be minimal. Optimally, 70% or more of the aerosolized volume should be available to the user.

The hand pulmonary delivery device is cordless, portable, and small enough to be held and operated with one hand. Preferably, the device is capable of delivering multiple daily doses over a period of at least 30 days without requiring a refill or other user intervention.

Figure 2:
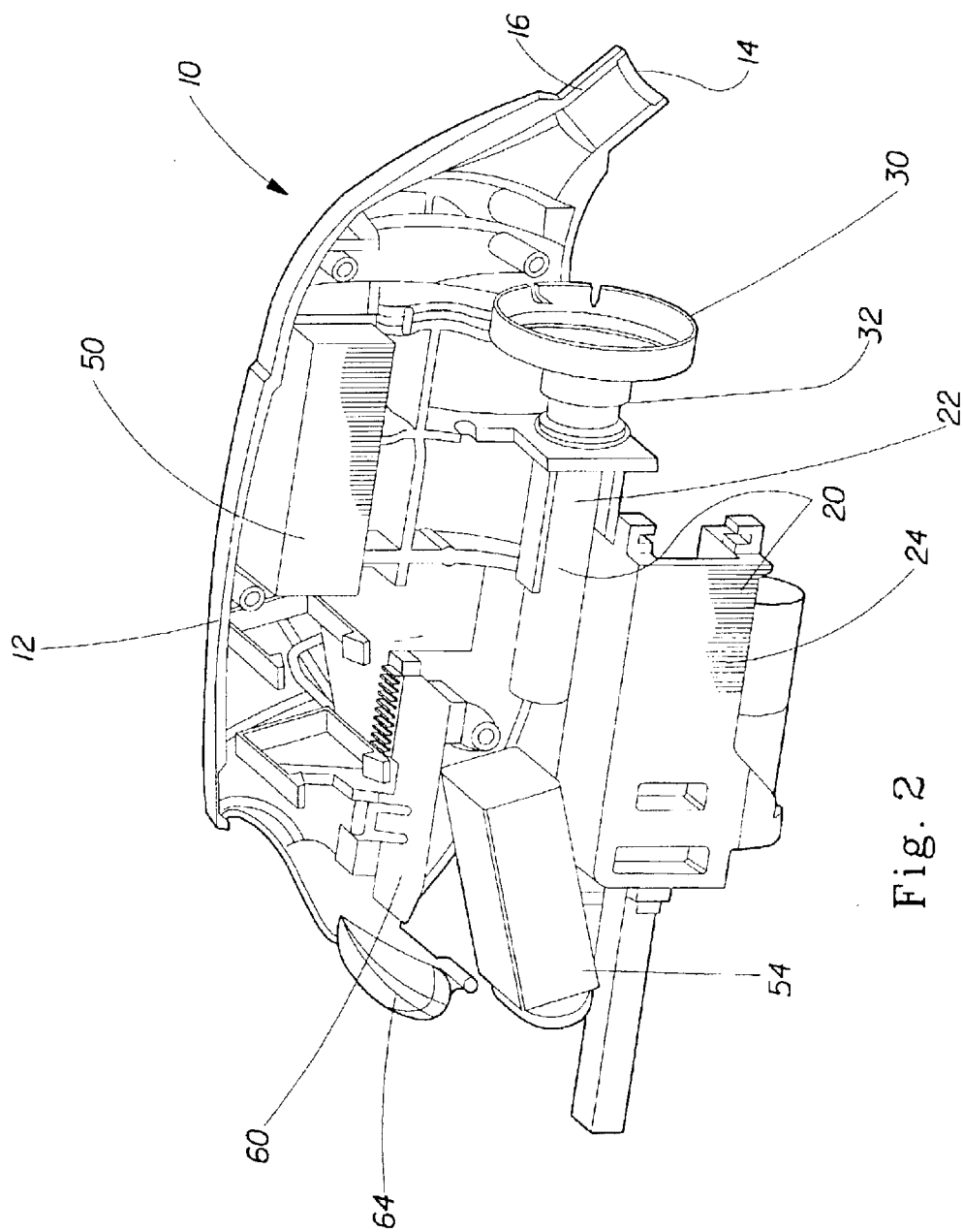
FIG. 2 is an exploded view of the device of FIG. 1.

The pulmonary delivery device 10 of the present invention, shown in FIGS. 1 and 2, includes a housing 12 sized so that it can be held in a user's hand. The housing 12 has an exit opening 14 for directing the aerosol to the user's mouth. The housing 12 encloses a dispensing system 20 for containing the liquid to be aerosolized and delivering it to an electrohydrodynamic apparatus 30, an electrohydrodynamic apparatus 30 for aerosolizing the liquid and delivering the aerosol to the exit opening 14, and a power supply 50 for providing a sufficient voltage to the electrohydrodynamic apparatus 30 to aerosolize the liquid. The device 10 may include a control circuit 60 that communicates with the dispensing system 20, the electrohydrodynamic apparatus 30, and the power supply 50.

Dispensing System

The dispensing system 20 holds the supply of the liquid to be aerosolized and delivers a single dose of the liquid to the electrohydrodynamic apparatus 30. The dispensing system 20 generally delivers the liquid to a single position in the nozzle 32 of the electrohydrodynamic apparatus 30. If the nozzle 32 has multiple spray sites 34 (shown in FIG. 3A), the nozzle 32 typically performs the function of distributing the liquid to the various spray sites 34, although it also would be possible for the dispensing system 20 to perform this function.

The dispensing system 20 includes a containment vessel 22 for containing and maintaining the integrity of the therapeutic liquid. The containment vessel 22 may take the form of a holder for a drug enclosed in single dose units, a plurality of sealed chambers each holding a single dose of the drug, or a vial for enclosing a bulk supply of the drug to be aerosolized. Bulk dosing generally is preferred for economic reasons except for liquids that lack stability in air, such as protein-based therapeutic agents.

The vessel 22 preferably is physically and chemically compatible with the therapeutic liquid including both solutions and microsuspensions and is liquid- and air-tight. Vessel 22 may be treated to give it antimicrobial properties to preserve the purity of the liquid contained in the vessel 22. The material of the vessel and any antimicrobial coating applied thereto are biocompatible.

The vessel 22 may be capable of maintaining the sterility of a sterile liquid placed therein. Preferably, vessel 22 is aseptically filled and hermetically sealed to maintain sterility of the therapeutic liquid during its shelf life. This may be accomplished, for example, using a "form, fill, seal" process or a "blow, fill, seal" process. The vessel 22 remains sealed until it is connected to the dispensing system 20 prior to the first use. After the first use, seals or check valves between the vessel 22 and the dispensing system 20 and unidirectional flow of the liquid maintain the integrity of the liquid in the vessel 22. In a preferred embodiment, vessel 22 is an easily collapsible thin pouch. The shape, collapsibility and outlet orifice of the pouch allow maximum withdrawal of a drug.

When bulk dosing is used, the dispensing system 20 includes a dose metering system 24 for withdrawing a predetermined, precise dose of the liquid from the containment vessel 22 and delivering this dose at a controlled flow rate to the nozzle 32 of the electrohydrodynamic apparatus 30. Preferably, the dose metering system 24 is capable of consistently metering the desired dose to within at least about ±10%, and more preferably ±5%, of the set dose volume.

The dose metering system 24 may comprise a piezoelectric pump (including, but not limited to, the pump described in copending U.S. patent application Ser. No. 220,310 titled "Piezoelectric Micropump," filed Dec. 23, 1998), a manually or mechanically operated piston pump, or a pressurized gas. For example, a small motor may be coupled to gears to rotate a screw that in turn depresses the plunger of a vial such as those customarily used for insulin.

Figure 5:
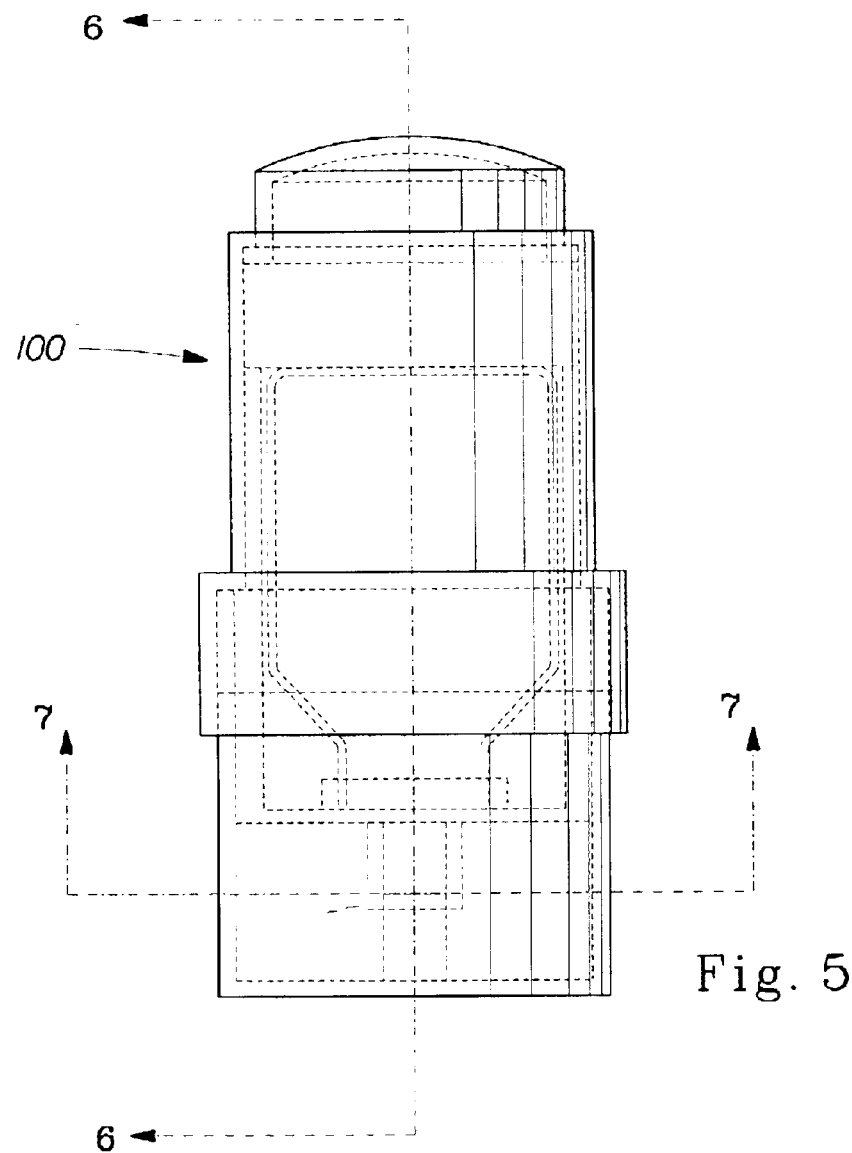
FIG. 5 is a side elevational view of a containment vessel and metering system useful in the device of the present invention.
Figure 7:
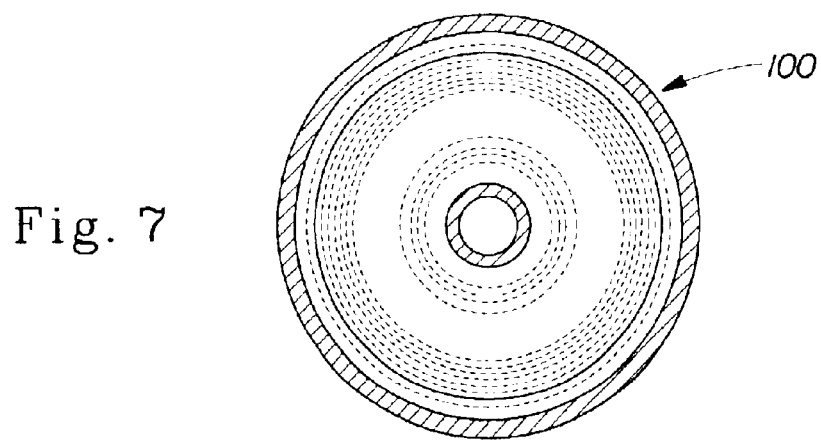
FIG. 7 is a cross-sectional view of the containment vessel and metering system of FIG. 5 along line C—C.
Figure 6:
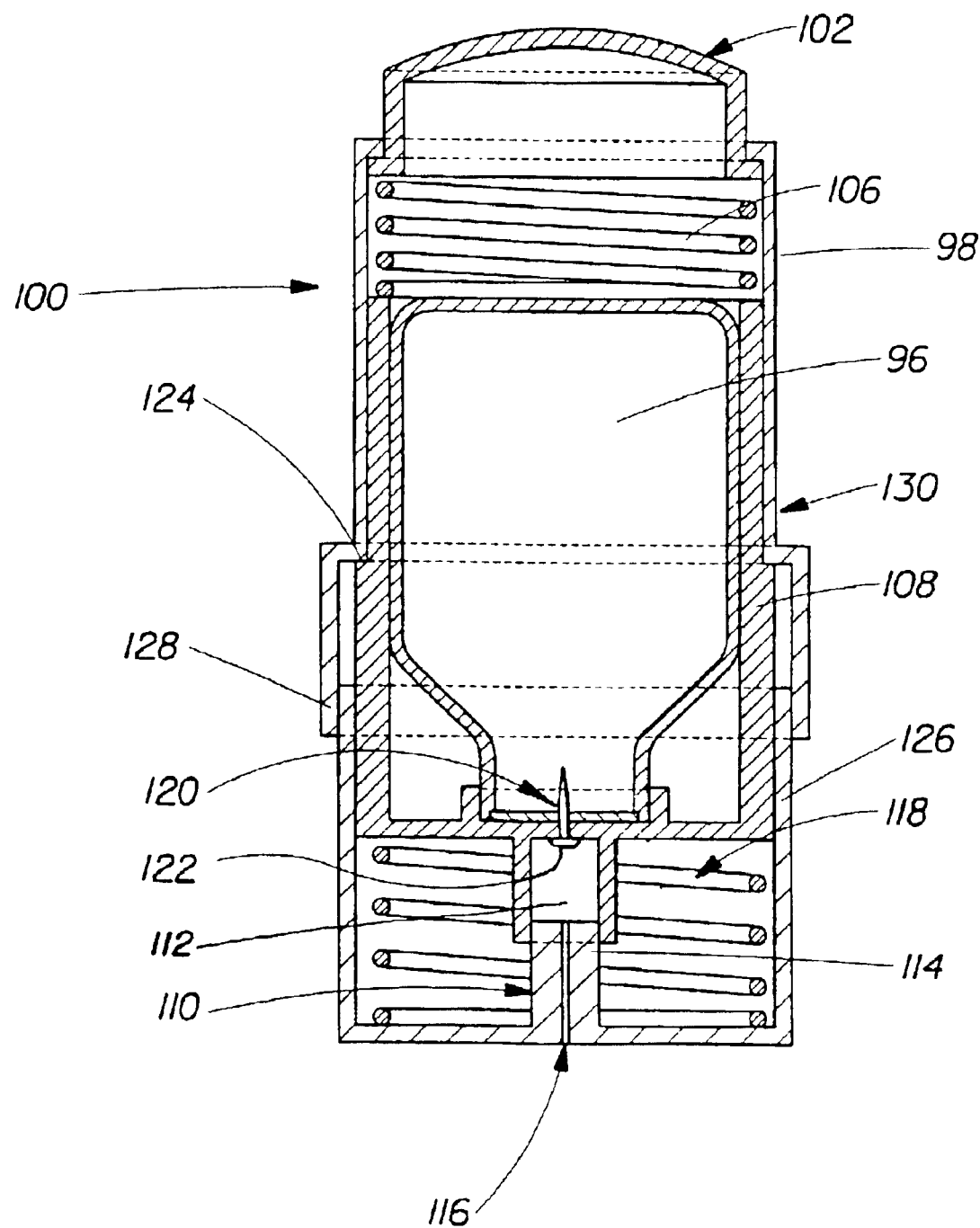
FIG. 6 is a cross-sectional view of the containment vessel and metering system of FIG. 5 along line B—B.

FIGS. 5–7 show a dispensing system 100 including a containment vessel 96 coupled with a manually actuated piston pump metering system 98. The pump 98 is actuated by depressing a button 102 that protrudes through the housing. Depressing the button 102 compresses button spring 106 against chamber housing 108, forcing the housing 108 downward. As the chamber housing 108 moves downward, liquid is forced from the chamber 112 below the housing 108 through capillary tube 114 and outlet check valve 116. The button 102 is held until chamber housing 108 is fully lowered.

When chamber housing 108 is fully lowered and the button 102 is released, the now compressed chamber housing spring 118, located below chamber housing 108, forces the chamber housing 108 upward. The vacuum formed in the chamber 112 as the housing 108 rises draws liquid into the chamber 112 from the containment vessel 96 through needle 120 and chamber check valve 122. Chamber housing 108 continues to rise until it reaches dose adjuster stop 124. The position of the dose adjuster 130 relative to the piston housing 126 limits the travel of the chamber housing 108, which controls the chamber volume (dose). The stop 124 may include a threaded or other suitable adjustment 128. Flow rate may be controlled by the spring rates of springs 106, 118. The piston 110 and check valves 116, 122 provide unidirectional liquid flow.

Returning to FIGS. 1 and 2, the pump or other metering system 24 may be formed from injection molded plastic or other suitable material. Preferably, this material will have antimicrobial properties or be coated with an antimicrobial coating. The material and antimicrobial coating of the metering system 24 are biocompatible. Passages within the metering system 24 that may contact liquid are compatible with the liquid, biocompatible, and of a design and size compatible with solutions and microsuspensions. The metering system 24 is actuated by the control circuit 60 as described below.

The material of the metering system 24 is compatible with sterilization techniques. Preferably, the metering system 24 will be packaged in a sterile condition to provide a sterile shelf life. As described above, after the first use, seals such as check valves 116, 122 and unidirectional liquid flow maintain the integrity of the liquid in the passages of the metering system 24.

The metering system 24 and control circuit 60 may cooperate to provide a dose counting function. The device 10 may include a dose display showing the doses administered and the doses remaining. The dispensing system 20 (and particularly the metering system 24) may cooperate with the control circuit 60 to limit the delivery of the liquid to predetermined times or intervals.

Electrohydrodynamic Apparatus

The electrohydrodynamic apparatus 30 functions by electrically charging the liquid to be aerosolized until the repulsive force of the charge overcomes the force of surface tension, causing the bulk liquid to be broken into minute droplets. The electrohydrodynamic apparatus 30' provides a sufficient volumetric flow rate of liquid so that a desired amount of a therapeutic liquid may be delivered during a user's inhalation of a single breath. This flow rate has not been achieved before in a hand-held inhaler 10. Preferred nozzles achieve aerosolization of particles in the respirable range at high flow using multiple spray sites in a compact configuration suitable for use in a hand-held device, with minimal wetting losses and arcing.

In electrohydrodynamically-generated aerosols, it generally is known that $$D_p \propto Q^{1/3}$$

where $D_p$ is the particle diameter and Q is flow rate. While spray tip geometry, its association with other electrodes, and the formulation characteristics affect the effective flow rate, stable Taylor cones and a high fraction of respirable particles can be maintained only if the flow rate per spray site is about 1 µL/sec or less. The number and configuration of spray sites therefore determines the maximum flow rate, i.e., the maximum amount of therapeutic liquid that may be delivered during a user's inhalation of a single breath.

A direct correlation between the mass median diameter (MMD) of the aerosol and the flow rate also has been observed. In general, if 80% or more of the particles are to have a diameter of 5 microns or less (as measured using either a Malvern Instruments Mastersizer® S or Model 2600 particle size spectrum analyzer), the flow rate per site likely will be less than or equal to about 1 $\mu$L/sec, more likely less than or equal to about 0.5 $\mu$L/sec. It is expected that delivery to a user's lungs of particles having this size distribution may be achieved at higher flow rates per site due to evaporation of the particles during delivery, particularly when the liquid includes a volatile solvent such as ethanol.

The device 10 is capable of spraying a wide range of formulations including liquid pharmaceutical solutions and suspensions. Small adjustments in the number of spray sites, volumetric flow rate, or the magnitude of the operating voltages may be required to tailor the device 10 to a specific formulation, but the basic design of the device 10 is expected to remain constant.

Figure 3A:
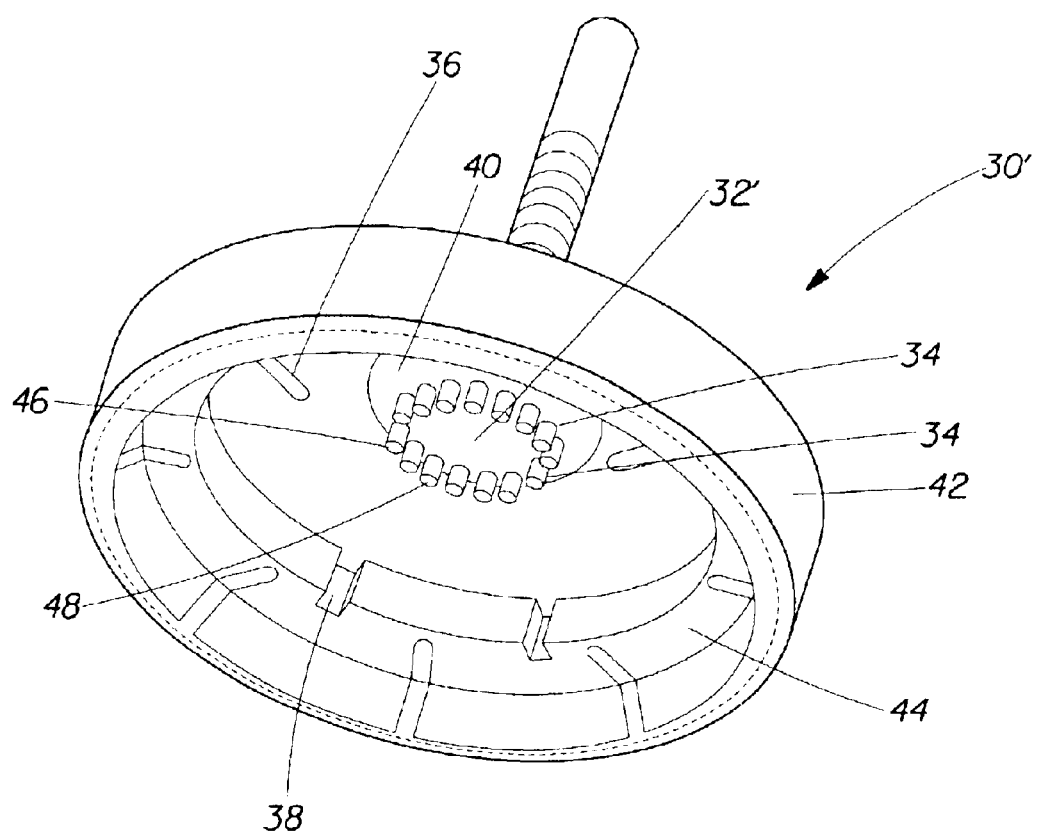
FIG. 3A is a detail view of a preferred nozzle useful in the device of the present invention.
Figure 3B:
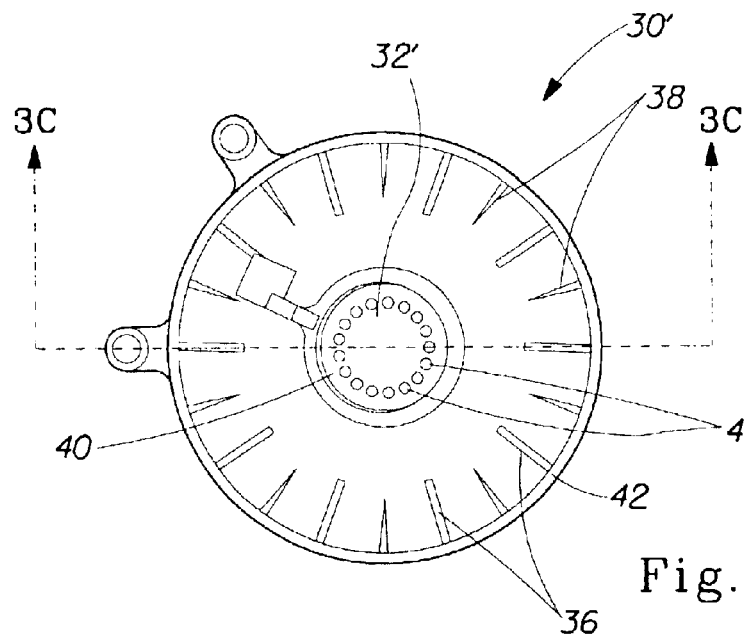
FIG. 3B is a bottom view of the nozzle of FIG. 3A.
Figure 3C:
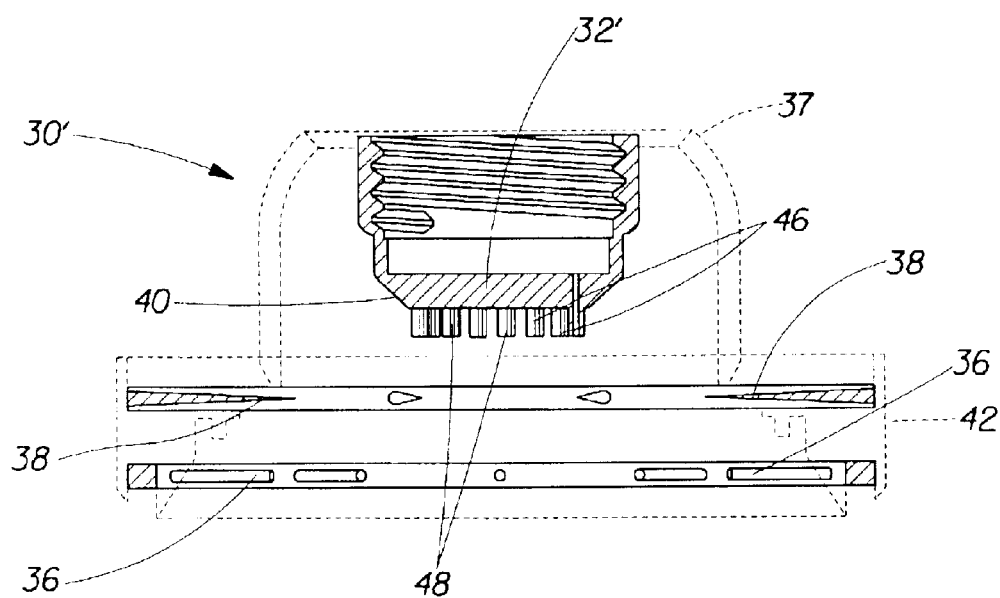
FIG. 3C is a cross-sectional view of the nozzle of FIG. 3B along line A—A.
Figure 4:
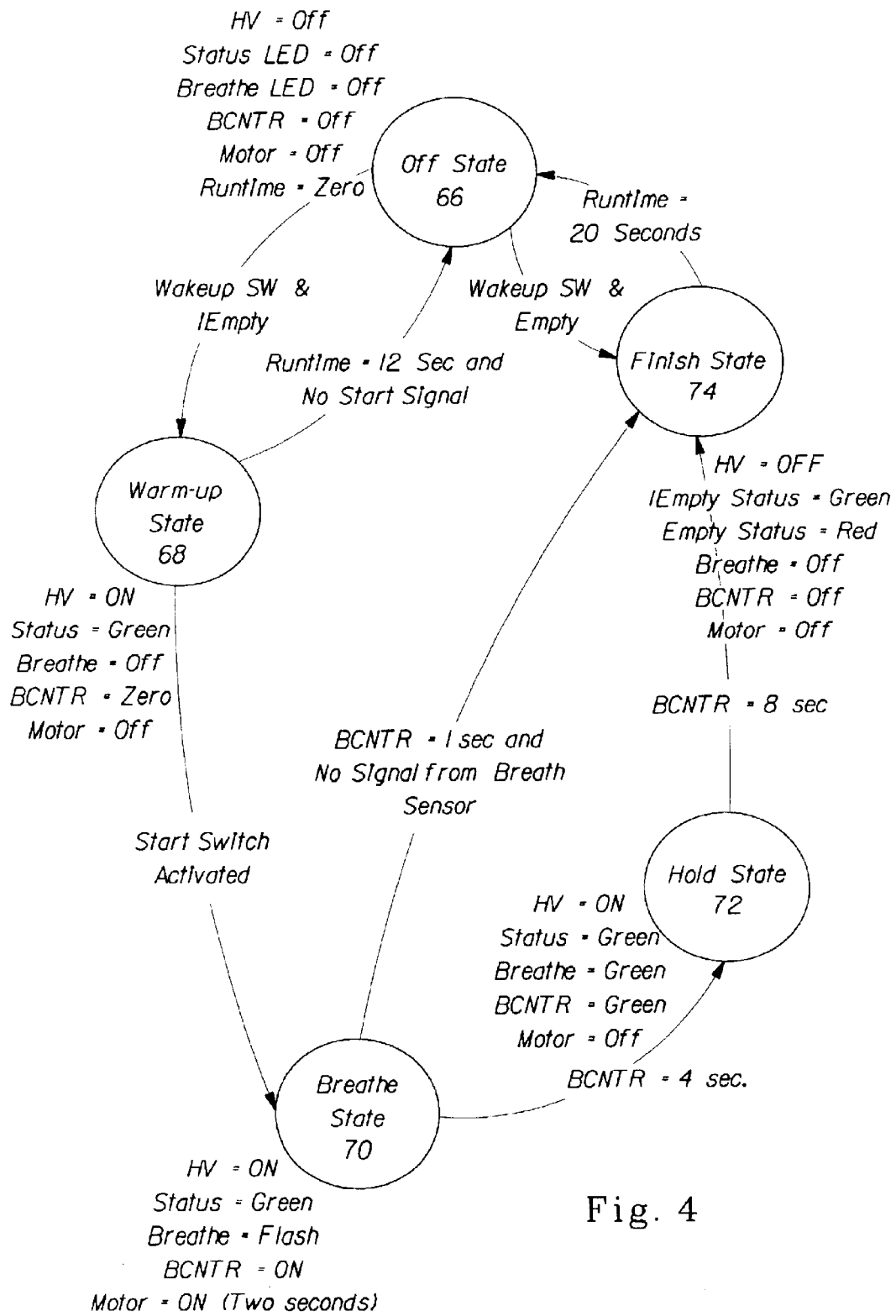
FIG. 4 is a state diagram showing the relationships among the operational states of an embodiment of the device of the present invention.

As shown in FIGS. 3A, 3B, and 3C, the electrohydrodynamic apparatus 30' includes a nozzle 32', at least one electrical reference electrode 36, and at least one neutralizing or discharge electrode 38. The nozzle 32' may include a base plate 40 and a skirt 42 extending downwardly from the base 40. Preferably, the nozzle 32' is located along the axis of a generally cylindrical nozzle housing.

A dielectric material 44 may be recessed within the skirt 42, as shown in FIG. 3A. Alternatively, the skirt 42 may be comprised of a dielectric material and the dielectric member 44 deleted. A flow director 37 may be provided as shown in FIG. 3C to aid in moving air past the nozzle 32 to sweep away the aerosol as described more fully in U.S. application Ser. No. 130,873, filed Apr. 23, 1999, which is fully incorporated herein by reference. The flow director 37 may be a discrete element or integral with the skirt 42.

The nozzle 32' includes a plurality of spray sites 34 oriented to deliver the spray toward a user's mouth, and particularly downstream toward the exit opening 14 of the housing 12 of a pulmonary aerosol delivery device 10. Preferably, the spray sites 34 are oriented vertically downward when the device is in use.

Any spray site 34 that supports formation of a Taylor cone may be used, such as capillary tubes, ball tips and conical tips. The spray sites 34 may be formed integrally with the nozzle 32', e.g., by machining or pressing. The nozzle 32' typically performs the function of distributing the liquid from the dispensing system 20 to the individual spray sites 34.

The preferred number and arrangement of spray sites 34 provided within the nozzle 32' may depend on the particular therapeutic agent or class of agents. Therapeutic agents that require high flow rates (i.e., up to about 50 $\mu$L in about 2 seconds) require multiple spray sites 34. When multiple spray sites 34 are used, the sites 34 should be positioned to reduce interaction among the spray sites 34 and between the spray sites 34 and the housing 12. For spray sites 34 oriented to spray vertically downward, circular arrangements of spray sites 34 are preferred.

In a preferred 17-spray site nozzle 32', the spray sites 34 may be parallel capillary tubes 46 extending from base 40. The tubes 46 are integral with a sprayer assembly having a single inlet port (not shown in the drawings). Thus, the 17-spray site nozzle 32' has built-in manifolding to distribute the liquid to the tubes 46, providing a nearly "instant" on and off feature when the metering system 24 is actuated and deactuated. The tube length may vary but preferably is at least about 0.003 inch.

The tubes 46 preferably are arranged in a circular pattern and spaced an equal distance from one another. The diameter of the circle is selected to be large enough to minimize the tendency to form a single large Taylor cone among the spray sites 34. For example, the circle may have a diameter of approximately 0.4–0.6 inches in a nozzle 32' intended for use in a hand-held device 10. The tubes 46 preferably are positioned close to the edge of the base 40. This reduces both interactions among the tube tips 48 and electrostatic shielding of the tips 48 by the portion of the base plate 40 that extends radially beyond the circle of the tips 48, which allows spraying of liquids with greater conductivities at a smaller potential than if the tips 48 were shielded. The preferred arrangement and position of spray sites 34 may vary for nozzles 32' with different types or numbers of spray sites 34.

Droplets having a neutral charge are preferred for pulmonary delivery. The electrohydrodynamic apparatus 30 therefore includes a charge neutralizer, in the form of a neutralizing or discharge electrode 38. The discharge electrode 38 provides a stream of ions having an opposite polarity from those in the aerosolized droplet cloud 59. The charged droplets engage the oppositely charged ions to form droplets having a neutral, or at least less polar, charge. Preferably, at least one of the plurality of discharge electrodes has a sufficient electric field strength to substantially neutralize a charge on the aerosolized droplets generated by a spray site. A dielectric material may be placed between the spray sites 34 and the discharge electrode 38 to modify the electric field and/or reduce the current draw of the electrohydrodynamic apparatus 30.

Discharge electrodes 38 aimed toward the sprayer axis may be positioned around the nozzle 32' downstream of the tip ends, preferably with the discharge electrodes 38 oriented radially inwardly and spaced equidistant from one another in the area of the tube tips 48. The number and position of neutralizing electrodes 38 may vary with the number and configuration of spray sites 34. Eight discharge electrodes 38 in the position illustrated have produced satisfactory results in the 17-spray site nozzle 32'.

A plurality of reference electrodes 36 is arranged downstream of the discharge electrodes 38, best shown in FIG. 3C, with the reference electrodes 36 aimed toward the axis. In a preferred nozzle 32', the reference electrodes 36 are oriented radially inwardly. The reference electrodes 36 may extend through slots in the dielectric material 44 below the discharge electrodes 38. Preferably, the number of reference electrodes 36 is equal to that of the discharge electrodes 38 such that the reference electrodes 36 may be positioned between and downstream of the discharge electrodes 38, best shown in FIG. 3B.

The reference electrodes 36 are maintained at a potential between that of the spray tip ends 48 and the discharge potential, which may but need not be true ground. It may be possible to obtain satisfactory results using reference electrodes that define a continuous ring rather than a plurality of individual reference electrodes 36. However, use of a plurality of reference electrodes 36 rather than a continuous ring and the interstitial positioning of the reference electrodes 36, provides superior resistance to wetting. The interstitial reference electrodes 36 also reduce arcing by virtually eliminating a liquid conductive path between the nozzle tips 48 and the reference electrodes 36. A current limiting resistor may be used to further control arcing.

The spray sites cooperate with a charge source sufficient to result in an electrohydrodynamic spray from at least one tip end. Preferably, each spray site 34 in the 17-spray site nozzle 32' produces a Taylor cone and forms an aerosol jet. The spray angle is not strictly downward but includes a radial component as a result of electrostatic interaction among the tube tips 48 which causes the sprays to repel one another. The radial component of the spray angle is not great enough to result in unacceptable losses from wetting of the housing 12. Wetting may be reduced by the use of a dielectric or some other material to modify the electric field. As described above, the skirt 42 may also be designed to control airflow streaming past the nozzle to control deposition of aerosol droplets and to stabilize the Taylor cone. Preferably, the edges of the tubes 46 are chamfered to improve Taylor cone formation.

A 17-spray site nozzle 32' with the above-described discharge configuration is capable of aerosolizing particles in the respirable range at a flow rate of up to about 20 $\mu$L/sec as measured with either a Malvern Instruments Mastersizer® S or Model 2600 particle size spectrum analyzer. The nozzle 32' is capable of spraying an aerosol of respirable particle size with a tight distribution at lower flow rates (7–10 $\mu$L/sec). At higher flow rates, a distinct knee may be observed at the high end of the distribution.

The 17-spray site nozzle 32' was tested in a delivery system consisting of a mouthpiece and a source of continuous controlled air flow. A 1% Triamcinolone formulation (in 80% ethanol/20% polyethylene glycol 300) was aerosolized at a flow rate of 15 $\mu$L/sec, with as particle size distribution of 4.9 microns MMD as measured by a Malvern Instruments Mastersizer® S particle size spectrum analyzer. At 10 $\mu$L/s, the distribution was monodispersed with a MMD of 3.7 microns. At 7 $\mu$L/s, the MMD was less than 3 microns, with 80% or more of the particles having a diameter less than 5 microns. Similar results were obtained with a 1% Albuterol free base formulation (in 80% ethanol/20% polyethylene glycol 300). Measurements with an Anderson cascade impactor confirmed all of the results achieved with the Mastersizer® analyzer.

Wicking losses, which may occur even when the electric field is off, must be controlled to allow both sustained operation of the device and delivery of the expected dose of the therapeutic liquid to a user. If uncontrolled, wicking may result in submersion of the nozzle and cessation of spray activity. Wicking losses are thought to result from the low surface tensions of the liquid formulations (as low as about 15 dynes/cm). To control wicking, the outer diameter of the spray sites 34 or other surfaces of interest may be coated with a low surface energy coating. Applying the critical surface energy concept pioneered by Zisman, a coating having a solid surface energy well below 15 dynes/cm should be selected. Fluorocarbon coatings having surface energies lower than that of Teflon (about 18 dynes/cm) are believed to be suitable for such use. When the tubes 46 of the 17-spray site nozzle 32' are coated with a low surface energy coating, the nozzle 32' is capable of spraying over 3,500 microliters of liquid with minimal accumulation at the base 40 of the tubes 46.

The conducting (electrode) components 34, 36, 38, 40 of the nozzle 32' may be fabricated from 303 or 316 stainless steel. Other suitable conductors also may be used as long as the material is compatible with the liquid to be sprayed, is resistant to corrosion, and does not deteriorate during the expected life of the device. The nonconducting components may be formed from machined Delrin, Lexan, or other suitable material.

Power Supply System

Electrospray nozzles 32 rely on high voltage to charge the formulation as it exits the spray site 34. The power supply system 50 is capable of providing a voltage capable of actuating the electrohydrodynamic apparatus 30 to produce an aerosol having desired characteristics with a minimum of arcing. Voltages in the range of about 2,600–6,000 V or more at very low amperages (less than about 100 microamperes, and preferably less than about 50 microamperes) generally appear to yield satisfactory results, although voltages outside this range may be suitable depending on the size of the device 10 and the type of electrohydrodynamic spray nozzle 32' used. The minimum voltage generally increases, for example, as the number of spray sites 34 increases. A nozzle 32 with the simplest geometry (i.e., four electrodes 38 and a single spray site 34) generally requires a minimum voltage of about 2,600 V. Typical voltages for nozzles 32' used in the present device 10 are in the range of about 4,000–5,000 V. Voltages above about 6,000 V generally are difficult to achieve in a hand-held device using conventional power supplies, but higher voltages (in the range of about 2,600–20,000 V) may be usable with power supply improvements.

The power supply 50 includes a high voltage DC to DC converter, preferably a transformer based switching converter. The DC to DC converter is connected to a battery 54, which may be included in the power supply 50. Alternatively, the battery 54 may be incorporated into the containment vessel 22 so that the supply of therapeutic liquid and the battery 54 may be replaced simultaneously.

Lithium batteries are preferred because of their energy density to volume ratio, their long shelf life and their voltage stability over their operating life. Other batteries such as alkaline batteries and rechargeable nickel metal hydride batteries (e.g., NiCad batteries) also may be used. The high voltage power supply 50 preferably has dual outputs with one output at positive DC voltage and the second output at negative DC voltage. The supply 50 also has a reference output, nominally at ground potential, that is common to both the positive and negative outputs. The anticipated output voltage range is ±5000 VDC, measured with respect to the reference output. Each of the dual outputs preferably has the same tolerance and operates to within about 2% of the nominal output voltage. The maximum allowable ripple for each of the dual outputs preferably is about 1%, measured with respect to the reference output.

The power supply 50 preferably can accept an input voltage over the range of about 6–9 VDC and generate a maximum output current for each of the dual outputs of about 100 microamperes. The supply 50 should be able to supply this maximum output current on both outputs simultaneously and continuously. The power supply 50 should not be damaged in any way if the outputs (one or both) are shorted to ground or shorted together for a duration of less than one minute and should resume normal operation if the short on the output is removed.

Practical limitations are imposed on the physical size of both the high voltage power converter and the battery 54 in a cordless hand-held unit 10. While commercially available DC-to-DC converters readily can accept input voltages of 12 or 24 VDC and generate outputs of 10 kV and higher, these converters are large and would be nearly impossible to package into a hand-held pulmonary delivery device. The voltage output of smaller converters often is limited to 3–6 kV. The battery size limits the energy available to the high voltage converter. To maintain the desired operating life of at least thirty days with multiple doses per day, operation of the nozzle 32' requires no more than about 1.0 watts and preferably no more than about 0.5 watts.

For the device 10 of the present invention, the target upper limit on the magnitude of the operating voltages for the nozzle 32' is 5 kV. Because the package size preferably is as small as is reasonably possible, the maximum physical envelope of the high voltage power converter preferably is about 2.0"×0.7"×0.6" (50.8 mm×17.8 mm×15.24 mm) and the maximum weight of the high voltage power converter preferably is about 30 grams (1 ounce).

The power supply 50 preferably is fully encapsulated using glass-filled epoxy or an equivalent conformal coating having the dielectric strength to allow tight packaging of the high voltage conversion circuitry into a small volume. Any wires emanating from the power supply modules 50 will have sufficient insulation to meet the requirements of EN60601 and UL2601 standards.

Control Circuit

The device 10 includes a control circuit 60 communicating with the dispensing system 20, the electrohydrodynamic apparatus 30, and the power supply system 50. The power supply system 50 may be integrated into the control circuit 60. Preferably, a single integrated circuit 60 such as a programmable logic device (PLD) controls all the functions of the device 10, which may include metering control, actuating devices, high voltage control, power save feature, status indicators, user inputs, dose counting and breath sensing. It is expected that the integrated circuit 60 can control all desired functions without software, but the device 10 also may perform effectively with a control circuit 60 including software.

The control circuit 60 includes an actuation device for initiating the flow of aerosolized liquid. The actuation device may include a sensor (not shown in the drawings) for detecting a user's inhalation of breath that cooperates with the electrohydrodynamic apparatus 30 to initiate the aerosol flow. For example, the breath sensor may be a flapper switch, a pressure transducer, or a piezoelectric or other air motion or air velocity detector. Alternatively, the actuation device may comprise a manual actuator 64 on the exterior of the housing 12.

In the manually-actuated device 10 (i.e., a device without a breath sensor), the control circuit 60 includes an On/Off button 62 and a Dosing button 64 or equivalent devices on the exterior of the housing 12. These actuators 62, 64 preferably are actuated easily by users with limited abilities.

The On/Off button 62 initially causes the control circuit 60 to actuate the high voltage supply 50, a shut-down timer and a self-priming feature. Actuation of the On/Off button 62 may be indicated by illumination of a power status indicator. The Dosing button 64 actuates the metering 24 or dispensing 22 control. Manual operation of the device 10 therefore requires two inputs from the user (or person assisting the user). The On/Off and Dosing buttons 62, 64 must be pressed in sequence for the dose to be delivered. If the buttons 62, 64 are pressed in the wrong order the device 10 will turn on but no drug will be delivered. Multiple actuations of either button 62, 64 within a specified interval are treated as a single actuation.

The operation of the device 10 may be accomplished by a series of timers and clocks that are inputs for a state machine. The device 10 steps from "state" to "state" as a result of clocked inputs, with the outputs determined by the operational "state" then in effect. The state machine may be implemented in a PLD control circuit 60 such that control signals to the various subsystems originate from the PLD 60.

In one potential control paradigm for a manually-actuated device 10, the state machine consists of five states as shown in FIG. 4. The Off or Power Save state 66 is the baseline state for the control system 60 when the device 10 is not functioning. In this state 66, the high voltage supply 50 is turned off and the current draw from the battery 54 is minimal.

The Warm-Up state 68 is entered when the user presses the On/Off button 62 and the drug vessel 22 is not empty. A status LED, visible on the exterior of the housing 12, illuminates green. The high voltage supply 50 and the shut down timer are turned on in this state 68. Self-priming, which causes the liquid to fill the residual nozzle volume and be delivered to the spray sites 34 so aerosolization can begin immediately upon actuation of the Dosing button 64 or a breath sensor, also is turned on in the Warm-Up state 68. The shut down timer ensures that if the Dosing button 64 is not pressed within a specified time after entering the Warm-Up state 68, for example, about 12 seconds, the device 10 will return to the Off state 66. A purge cycle may be carried out before the device 10 returns to the Off state 66 to expel from the device 10 the unused liquid supplied to the electrohydrodynamic apparatus 30 during self-priming.

Actuation of the Dosing button 64 while the device 10 is in the Warm-Up state 68 (e.g., within about twelve seconds of pressing the On/Off button 62), causes the control system 60 to enter the Breathe state 70. Actuation of the Dosing button 64 is associated with a flashing green breath prompt indicator followed by the solid green indicator display during the breath hold period. The device 10 will not respond to actuation of the Dosing button 64 until the previous dosing cycle is completed. The allowed interval between doses may be preset to allow or prohibit administration of sequential doses.

In the Breathe state 70, the metering control system 24 is activated for approximately two seconds to deliver drug to the nozzle 32. This causes the nozzle 32 to begin aerosolizing the drug immediately. After about four seconds, the control system 60 exits this state 70 and enters the Hold state 72. Once in the Hold state 72, the device 10 will wait about four additional seconds to allow any remaining material on the nozzle 32 to be aerosolized before entering the Finish state 74. (If a breath sensor is present, the device enters the Finish state 74 if there is no signal from this sensor after being in the Breathe state 72 for about one second.)

Once the control system 60 enters the Finish state 74, the high voltage supply 50 is turned off. If the device 10 includes a purge cycle for emptying unused or residual liquid from the electrohydrodynamic apparatus 30, this cycle may be actuated in the Finish state 74. The control system 60 stays in the Finish state 74 until the run-time counter reaches about twenty seconds. Once the run-time counter times out, all status indicators are turned off and the control system 60 returns to the Off state 66.

As described above, the control circuit 60 may communicate with and control the metering system 24 by PLD output in response to actuation of the Dosing button 64. The control circuit 60 may have a memory for storing dose information, which may then be provided to the metering system 24. Drug dosing within the hand-held device 10 can be implemented with a variety of mechanisms such as those described above.

For a motor-driven metering system, the PLD activates the motor for about the first two seconds of the Breathe state in the dosing cycle. Dose volume is determined by the gearing of the motor and the voltage that is applied to the motor. Both are held constant in the current design and yield, for example, a 20 $\mu$l dose. For a piezoelectric micropump, the PLD output forms a pulse train that is applied to the piezoelectric valves that make up the pump. The timing within the pulse train provides the proper valve actuation for pumping.

The high voltage power supply 50 may be actuated by a simple on/off function controlled by the PLD 60. The magnitude of the high voltage output is determined by the design of the power supply 50 and cannot be altered by the user or clinician. In a preferred embodiment, the high voltage supply 50 becomes active upon actuation of the On/Off button 62. During a normal operating cycle in which the Dosing button 64 is depressed and drug is delivered, the high voltage supply 50 is active for about twenty seconds. If the Dosing button 64 is not depressed, the high voltage power supply 50 is deactivated after about twelve seconds.

The control circuit 60 preferably will include indicators to display the device status, which may, for example, comprise LED indicators. A preferred combination and arrangement of LEDs is described. Other combinations and arrangements of indicators (including indicators made from components other than LEDs) also may be used to accomplish the same objectives.

A preferred embodiment includes a two-LED combination (not shown in the drawings) in which one LED is a power status indicator and the other is a breath prompt signal. The power status LED preferably indicates a single color, preferably green. This indicator follows the same operating cycle as the high voltage power supply 50: the indicator is illuminated when the On/Off button 62 is actuated and remains illuminated while the high voltage power supply 50 is active. Illumination of the power status LED indicates that the device 10 is ready for normal operation.

The breath prompt LED preferably indicates each of three operational states for the device 10: Breathe, Hold Breath, and Unit Empty. This may be accomplished, for example, using an LED that is capable of flashing green, solid green, and solid yellow indications. The flashing green is displayed when the device 10 enters in the Breathe state 70 and continues for about four seconds. The flashing green alerts the user that the drug is being delivered and that the user should breathe in deeply while the flashing green is displayed.

The solid green indication appears after the flashing green indication is complete and lasts about four seconds. The solid green alerts users to hold their breath for a short time after inhaling of the aerosolized liquid to promote retention of the aerosol in the lungs for a long enough time for effective liquid absorption.

The solid yellow indicator is illuminated any time the device 10 is activated (e.g., by pressing the Dosing button 64) after the last dose is delivered. The solid yellow indicates to the user that the vessel 22 is empty and maintenance is required. Preferably, dose status is controlled by a signal from a dose counter. Dose counting may be implemented using the PLD 60 or other means such as a mass or volume sensor in the vessel 22. When the PLD 60 is used, the dose count is incremented upon completion of a dosing cycle. When the dose count reaches a preset limit, the device 10 indicates an empty vessel 22 by displaying the solid yellow LED display and will no longer function. After the device is serviced, the dose counter may be reset and normal operation cycles may be resumed.

The control circuit 60 may have a memory for recording dose information and/or dose history. The control circuit 60 may communicate with metering system 24, for example, by sending dose information stored in its memory to the metering system 24. The metering system 24 in turn may send dose history information to the control circuit 60 for storage in its memory.

The device 10 preferably includes a breath sensor to determine if proper inhalation was occurring during spraying. The PLD 60 may monitor the status of the breath sensor. If no breath is sensed one second after the Dosing button 62 is actuated, the PLD 60 will signal the high voltage power supply 50 and the metering system 24 to shut down and drug delivery will cease.

In a particularly preferred embodiment, the device 10 is actuated by a user's breath rather than a Dosing button 64 to optimize intake of the aerosol by a user. In this preferred operational mode, the device 10 primes itself upon actuation of the On/Off button 62 by moving liquid to the spray site tips 48 so that drug delivery can begin immediately upon actuation of the Dosing button 64. The flow of the aerosol is actuated by a users inhalation of breath, eliminating the need for the user to coordinate his or her breathing with actuation of the device 10. To accomplish this, the actuation device comprises a breath sensor that cooperates with the electrohydrodynamic apparatus 30 to initiate the aerosol flow. The sensor also may detect a multiple breaths by a user and cooperate with the control circuit 60 to display this on a multiple breath indicator. If desired, a manual actuator such as Dosing button 64 may be provided in addition to the breath sensor.

A lockout (not shown in the drawings) cooperating with a keypad, smart ring, magnetic ring, or the like may be incorporated into the control circuit 60 to prevent use by an unauthorized user. The device 10 also may include a position sensor that prevents operation of the device 10 unless the electrohydrodynamic apparatus 30 is in a predetermined (e.g., vertical) orientation.

The control circuit 60 may include a timer that cooperates with the dispensing system 20 to limit the delivery of the liquid to predetermined times or time intervals. The timer also may provide a signal to alert the user, by a display or alarm, that a dose is due.

Housing

The housing 12 preferably is constructed from a durable, easily cleanable, nonconductive, biocompatible, inexpensive material compatible with the liquid to be aerosolized, such as polyethylene or polypropylene, although other suitable materials also may be used. The material may be treated so that it has antimicrobial properties or provided with a biocompatible antimicrobial coating to assist in controlling the growth of microorganisms in and on the housing.

Typically, the housing 12 has a generally cylindrical or oblong shape that allows the electrohydrodynamic apparatus 30 to be in a substantially vertical position during use, but other housing shapes also may be used. The housing 12 preferably is streamlined so it may be stored conveniently in a shirt pocket, purse, or other small space.

The housing 12 defines an exit opening 14, generally positioned on a lower side wall. The exit opening 14 may include a mouthpiece 16 or collar extending from the housing 12 to assist in directing the aerosolized liquid to the user's mouth. The mouthpiece 16 may be formed integrally with the housing 12 or provided as a separate piece that slides or pivots into position when needed.

The housing 12 is molded or otherwise shaped so a user easily may grasp the housing 12 and position it so that the exit opening 14 is directed toward the user's mouth. Preferably, the housing 12 has rounded edges so a user may grasp it comfortably. Ridges may be provided on the housing 12 to guide the placement of a user's fingers.

The device 10, including the housing 12 and the mouthpiece 16, must transport the maximum amount of aerosol droplets to the user. Losses of aerosol droplets within the housing 12 will result in delivery of a lower than expected dose of the therapeutic agent to the user. The electrohydrodynamic apparatus 30 should be positioned within the housing 12 to reduce wetting losses. With the 17-spray site nozzle 32', positions away from the back wall of the elbow between the housing 12 and the mouthpiece 16 are preferred. The 17-spray site nozzle 32' achieved transport efficiencies in the range of about 76–93 percent with an average transport efficiency of about 83 percent.

In addition to wicking losses, substantial losses may result from droplet deposition on the mouthpiece walls. In the present arrangement, the nozzle 32' sprays vertically downwards and the spray must be turned through an angle between 45 and 90 degrees in the mouthpiece 16 to reach the user. Droplet deposition on mouthpiece walls as the spray turns through this angle tends to result from the complex flow pattern in the bend that carries droplets towards the walls (with large droplets impacting the wall because of their inertia and small droplets diff-using to the wall by fluid turbulence) and turbulence produced in the flow, especially near the spray sites 34, which increases droplet diffusion to the wall.

Losses from droplet deposition on the mouthpiece walls may be controlled by careful design of the mouthpiece shape and airflow dynamics through the mouthpiece 16. The interior of the housing 12 should be shaped to allow natural convection currents to aid in moving the aerosol cloud out of the housing 12. An air inlet (not shown in the drawings) may be provided in the housing 12 in the area of the spray sites 34 to promote discharge of the aerosolized particles. The inlet to the mouthpiece 16 should be sized to assist in moving the spray around the bend and toward the exit opening 14.

Substantial losses from droplet deposition on or near the electrodes also may occur. These losses may be controlled by nozzle placement and geometry. The nozzles described above result in an acceptable level of losses at or near the electrodes.

The pulmonary delivery device 10 of the present invention may be either disposable or reusable. A disposable unit 10 may have a battery 54 and containment vessel 22 filled with the applicable therapeutic agent sealed within housing 12. The disposable unit 10 could provide, for example, a 30-day supply of a therapeutic agent, depending on such factors as the volume of therapeutic agent and its stability. The disposable unit 10 may include a dose counter with an indicator to signal that all doses have been expended.

A reusable unit 10 may be provided with an initial supply of a therapeutic agent within the containment vessel 22 and a battery 54. The housing 12 may comprise at least two interlocking mating segments so that it may be disassembled to refill the containment vessel 22 or replace the battery 54. The battery 54 may be incorporated into the vessel 22 for more convenient refills.

The reusable unit 10 also may include enhancements such as electronic features. These features may include, for example, dose reminder, dose counter and dose indicator. The unit 10 also may include a lockout cooperating with a timer to prevent overdoses or a lockout to prevent use by an unauthorized person.

Methods of Aerosol Administration

The invention also includes a method for oral administration of an aerosolized liquid therapeutic agent, which includes the steps of storing the liquid in a containment vessel 22, dispensing the liquid from the containment vessel 22 to an electrohydrodynamic apparatus 30, and electrically actuating the electrohydrodynamic apparatus 30 to aerosolize the liquid. The electrical actuation step may be initiated by a user's inhalation of breath.

The method also may include the steps of metering a desired amount of liquid to be dispensed from the containment vessel 22 to the electrohydrodynamic apparatus 30 and enclosing the containment vessel 22 and electrohydrodynamic apparatus 30 within a cordless housing 12 that can be held in a user's hand, the housing 12 including an exit opening 14 for directing the aerosol to the user's mouth. The method of the present invention further may include the step of neutralizing the electrical charge imparted to the aerosolized liquid by the electrohydrodynamic apparatus 30.

The preferred embodiment of this invention can be achieved by many techniques and methods known to persons who are skilled in this field. To those skilled and knowledgeable in the arts to which the present invention pertains, many widely differing embodiments will be suggested by the foregoing without departing from the intent and scope of the present invention. The descriptions and disclosures herein are intended solely for purposes of illustration and should not be construed as limiting the scope of the present invention which is described by the following claims.

What is claimed is:

1. A pulmonary aerosol delivery device, comprising:
   a housing of such size that the housing can be held in a user's one hand, the housing having an exit opening for directing an aerosol to a user's mouth;
   a containment vessel holding a liquid to be aerosolized;
   an electrohydrodynamic apparatus for aerosolizing the liquid and delivering the aerosolized liquid to the exit opening;
   a power supply for providing sufficient voltage to the electrohydrodynamic apparatus to aerosolize the liquid; and
   a dispensing system for delivering the liquid to be aerosolized from the containment vessel to the electrohydrodynamic system, the containment vessel, the electrohydrodynamic apparatus, the power supply, and the dispensing system being enclosed within the housing.

2. A pulmonary aerosol delivery device, comprising a housing of such size that the housing can be held in a user's one hand, the housing having an exit opening for directing an aerosol to a user's mouth and including therein:
   a dispensing system for containing a liquid to be aerosolized and delivering the aerosolized liquid to an apparatus for aerosolizing the liquid;
   an apparatus for aerosolizing the liquid and delivering the aerosolized liquid to the exit opening, the apparatus comprising
   a base;
   a plurality of spray sites each having a base end connected to the base and a tip end, an electrohydrodynamic spray being formed from at least one tip end when the liquid is caused to flow over the spray sites and the plurality of spray sites is placed in electrical communication with a power source;
   a plurality of discharge electrodes connected to the base, the plurality of discharge electrodes being spaced further from the base than the tip ends; and
   a plurality of reference electrodes connected to the base, the reference electrodes being spaced further from the base than the discharge electrodes;
   and
   a power supply system for providing sufficient voltage to the aerosolizing apparatus to aerosolize the liquid.

3. An apparatus for aerosolizing a liquid, comprising:
   a base;
   a plurality of spray sites each having a base end connected to the base and a tip end, an aerosolized spray being formed from at least one tip end when a liquid is caused to flow over the spray sites and the plurality of spray sites is placed in electrical communication with a charge source;

a plurality of discharge electrodes connected to the base, the plurality of discharge electrodes being spaced further from the base than the tip ends; and a plurality of reference electrodes connected to the base, the reference electrodes being spaced further from the base than the discharge electrodes.

4. The apparatus of claim 3, further comprising:

a charge source for charging the plurality of spray sites sufficiently to result in an electrohydrodynamic spray from a least one tip end.

5. The apparatus of claim 3, wherein the plurality of discharge electrodes and the plurality of reference electrodes are oriented toward the aerosolized spray.

6. The apparatus of claim 5, wherein the plurality of discharge electrodes and the plurality of reference electrodes are oriented radially toward an axis defined by the base end and tip end of one of the plurality of spray sites.

7. The apparatus of claim 6, wherein the plurality of discharge electrodes are spaced equidistant from one another and the plurality of reference electrodes are located in the interstices between the discharge electrodes.

8. The apparatus of claim 7, further comprising:

a dielectric material between the plurality of discharge electrodes and the plurality of reference electrodes.

9. The apparatus of claim 8, wherein the reference electrodes extend through slots provided in the dielectric material.

10. The apparatus of claim 3, wherein at least one of the plurality of spray sites has a sufficient electric field strength that when a liquid is caused to flow over said spray site, a net electrical charge is imparted to the surface of the liquid flowing over said spray site, the charge imparted to the liquid surface initially balancing the surface tension of the liquid to cause the liquid to form a cone adjacent to the spray site with the cone tip extending away from the spray site, the charge imparted to the surface eventually overcoming the surface tension of the liquid in the region of the cone tip to generate a thin jet of liquid that breaks into an aerosolized liquid consisting substantially of droplets of respirable size.

11. The apparatus of claim 10, wherein at least one of the plurality of discharge electrodes has a sufficient electric field strength to substantially neutralize a charge on the droplets generated by said spray site.

12. The apparatus of claim 3, wherein at least one of the plurality of spray sites has a sufficient electric field strength that when a liquid is caused to flow over said spray site, a net electrical charge is imparted to the surface of the liquid flowing over said spray site, the charge imparted to the liquid surface causing the liquid to form a cone adjacent to the spray site with the cone tip extending away from the spray site and then generate a thin jet of liquid in the region of the cone tip that breaks into an aerosolized liquid consisting substantially of droplets of respirable size.

13. An apparatus for aerosolizing a liquid, comprising:

a tubular base having a generally circular cross-section;

a plurality of spray sites each having a base end connected to the base and a tip end extending axially into a first end of the base, an aerosolized spray being formed from at least one tip end when the liquid is caused to flow over the spray sites and the plurality of spray sites is placed in electrical communication with a charge source;

a plurality of discharge electrodes each connected to the interior of the base at a distance further from the first base end than the spray site tip ends; and a plurality of reference electrodes each connected to the interior of the base at a distance further from the first base end than the plurality of discharge electrodes.

14. The apparatus of claim 13, further comprising:

a charge source for charging the plurality of spray sites sufficiently to result in an electrohydrodynamic spray from at least one tip end.

15. The apparatus of claim 13, wherein the plurality of discharge electrodes and the plurality of reference electrodes are oriented toward the aerosolized spray.

16. The apparatus of claim 13, wherein the plurality of discharge electrodes are located in the area of the tip ends of the plurality of spray sites.

17. The apparatus of claim 16, wherein at least one of the plurality of discharge electrodes has a sufficient electric field strength to substantially neutralize a charge on the droplets generated by said spray site.

18. The apparatus of claim 13, wherein at least one of the plurality of spray sites has a sufficient electric field strength that when a liquid is caused to flow over said spray site, a net electrical charge is imparted to the surface of the liquid flowing over said spray site, the charge imparted to the liquid surface initially balancing the surface tension of the liquid to cause the liquid to form a cone adjacent to the spray site with the cone tip extending away from the spray site, the charge imparted to the surface eventually overcoming the surface tension of the liquid in the region of the cone tip to generate a thin jet of liquid that breaks into an aerosolized liquid consisting substantially of droplets of respirable size.

19. The apparatus of claim 13, wherein the plurality of reference electrodes and the plurality of discharge electrodes extend radially inwardly toward an axis defined by the base end and tip end of one of the plurality of spray sites.

20. The apparatus of claim 19, wherein the plurality of discharge electrodes are spaced equidistant from one another and the plurality of reference electrodes are located in the interstices between the discharge electrodes.

21. The apparatus of claim 13, further comprising:

a dielectric material within the base between the discharge electrodes and the reference electrodes.

22. The apparatus of claim 21, wherein the reference electrodes extend through slots provided in the dielectric material.

23. The apparatus of claim 13, wherein the plurality of spray sites are arranged in a generally circular pattern.

24. An apparatus for aerosolizing a liquid, comprising:

a base plate having upper and lower surfaces each defining a generally circular perimeter;

a plurality of spray sites arranged in a circular pattern along the perimeter of the lower surface of the base plate, each of the spray sites having a base end mounted to the base plate and a tip end, an aerosolized spray being formed from at least one tip end when a liquid is caused to flow over the spray sites and the plurality of spray sites is placed in electrical communication with a charge source;

a skirt extending downward from the base plate;

a dielectric material enclosed by the skirt;

a plurality of discharge electrodes extending from the skirt at a distance further from the base plate than the spray site tip ends; and a plurality of reference electrodes each extending from the skirt at a distance further from the base plate than the discharge electrodes.

25. The apparatus of claim 24, wherein the dielectric material is a discrete member provided within the skirt.

26. The apparatus of claim 24, wherein the skirt is comprised of a dielectric material.

27. The apparatus of claim 24, wherein the plurality of reference electrodes are positioned in interstices between the discharge electrodes.

28. The apparatus of claim 24, wherein the plurality of discharge electrodes are spaced equidistant from one another and the plurality of reference electrodes are located in the interstices between the discharge electrodes.

29. The apparatus of claim 28, wherein the reference electrodes extend through slots provided in the dielectric material.

30. The apparatus of claim 24, wherein at least one of the plurality of spray sites has a sufficient electric field strength that when a liquid is caused to flow over said spray site, a net electrical charge is imparted to the surface of the liquid flowing over said spray site, the charge imparted to the liquid surface initially balancing the surface tension of the liquid to cause the liquid to form a cone adjacent to the spray site with the cone tip extending away from the spray site, the charge imparted to the surface eventually overcoming the surface tension of the liquid in the region of the cone tip to generate a thin jet of liquid that breaks into an aerosolized liquid consisting substantially of droplets of respirable size.

31. The apparatus of claim 30, wherein at least one of the plurality of discharge electrodes has a sufficient electric field strength to substantially neutralize a charge on the droplets generated by said spray site.

32. A pulmonary aerosol delivery device, comprising a housing of such size that the housing can be held in a user's one hand, the housing having an exit opening for directing an aerosol to a user's mouth and including therein:
   a dispensing system for containing a liquid to be aerosolized and delivering the liquid to an electrohydrodynamic apparatus;
   an electrohydrodynamic apparatus for aerosolizing the liquid and delivering the aerosolized liquid to the exit opening; and
   a power supply system comprising a battery and a DC to DC high voltage converter for providing sufficient voltage to the electrohydrodynamic apparatus to aerosolize the liquid.

33. The device of claim 32, wherein the device is cordless.

34. A pulmonary aerosol delivery device, comprising a housing of such size that the housing can be held in a user's one hand, the housing having an exit opening for directing an aerosol to a user's mouth and including therein:
   a dispensing system for containing a liquid to be aerosolized and delivering the liquid to an electrohydrodynamic apparatus;
   an electrohydrodynamic apparatus for aerosolizing the liquid and delivering the aerosolized liquid to the exit opening, the exit opening being moveable to assist in directing the aerosolized liquid to a user's mouth; and
   a power supply system for providing sufficient voltage to the electrohydrodynamic apparatus to aerosolize the liquid.

35. An apparatus for aerosolizing a liquid, comprising:
   a base;
   a plurality of spray sites each having a base end connected to the base and a tip end oriented vertically downward from the base, an aerosolized spray being formed from at least one tip end when a liquid is caused to flow over the spray sites and the plurality of spray sites is placed in electrical communication with a charge source;
   a plurality of discharge electrodes connected to the base, the plurality of discharge electrodes being spaced further from the base than the tip ends; and
   a plurality of reference electrodes connected to the base, the reference electrodes being spaced further from the base than the discharge electrodes.

36. An apparatus for aerosolizing a liquid, comprising:
   a tubular base having a generally circular cross-section and a first end;
   a plurality of spray sites each having a base end connected to the base and a tip end oriented vertically downward and extending axially into the first end of the base, an aerosolized spray being formed from at least one tip end when the liquid is caused to flow over the spray sites and the plurality of spray sites is placed in electrical communication with a charge source;
   a plurality of discharge electrodes each connected to the interior of the base at a distance further from the first base end than the spray site tip ends; and
   a plurality of reference electrodes each connected to the interior of the base at a distance further from the first base end than the plurality of discharge electrodes.

37. An apparatus for aerosolizing a liquid, comprising:
   a tubular base having a generally circular cross-section and a first end;
   a plurality of spray sites each having a base end connected to the base in a predetermined pattern and a tip end extending axially into the first end of the base, an aerosolized spray being formed from at least one tip end when the liquid is caused to flow over the spray sites and the plurality of spray sites is placed in electrical communication with a charge source;
   a plurality of discharge electrodes each connected to the interior of the base at a distance further from the first base end than the spray site tip ends; and
   a plurality of reference electrodes each connected to the interior of the base at a distance further from the first base end than the plurality of discharge electrodes.

38. A pulmonary aerosol delivery device, comprising a housing of such size that the housing can be held in a user's one hand, the housing having an exit opening for directing an aerosol to a user's mouth and including therein:
   a dispensing system for containing a liquid to be aerosolized and delivering the liquid to an electrohydrodynamic apparatus;
   an electrohydrodynamic apparatus for aerosolizing the liquid and delivering the aerosolized liquid to the exit opening; and
   a power supply system for providing sufficient voltage to the electrohydrodynamic apparatus to aerosolize the liquid;
   wherein the housing has antimicrobial properties.

39. An apparatus for aerosolizing a liquid, comprising:
   a base;
   a plurality of spray sites arranged in a generally circular pattern, each of the plurality of spray sites having a base end connected to the base and a tip end oriented vertically downward from the base, an aerosolized spray being formed from at least one tip end when a liquid is caused to flow over the spray sites and the plurality of spray sites is placed in electrical communication with a charge source;
   a plurality of discharge electrodes connected to the base, the plurality of discharge electrodes being spaced further from the base than the tip ends; and
   a plurality of reference electrodes connected to the base, the reference electrodes being spaced further from the base than the discharge electrodes.

40. The apparatus of claim 39, wherein the plurality of spray sites are spaced equidistant from one another.

41. The apparatus of claim 39, wherein the tip end of at least one of the plurality of spray sites is chamfered.

42. The apparatus of claim 39, wherein the exterior of at least one of the plurality of spray sites is coated with a material having a low surface energy.

* * * * *

UNITED STATES PATENT AND TRADEMARK OFFICE
CERTIFICATE OF CORRECTION

PATENT NO. : 6,796,303 B2
DATED : September 28, 2004
INVENTOR(S) : Williams C. Zimlich Jr. et al.

It is certified that error appears in the above-identified patent and that said Letters Patent is hereby corrected as shown below:

Title page,
Item [75], fourth inventor, should read -- Gahanna --.

Column 2,
Line 23, "users" should read -- user's --.

Signed and Sealed this

Fifteenth Day of February, 2005

JON W. DUDAS
*Director of the United States Patent and Trademark Office*